US011179099B2

(12) United States Patent
Colbaugh et al.

(10) Patent No.: US 11,179,099 B2
(45) **Date of Patent: *Nov. 23, 2021**

(54) REVERSE DUAL POSITIVE AIRWAY PRESSURE CHALLENGES FOR BREATHING DISORDER DIAGNOSTICS

(71) Applicant: KONINKLIJKE PHILIPS N.V., Eindhoven (NL)

(72) Inventors: Michael Edward Colbaugh, Level Green, PA (US); Lauren Elizabeth Hueser, Brighton, MA (US); Surya Subrahmanya Sreeram Vissapragada Venkata Satya, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

This patent is subject to a terminal disclaimer.

(21) Appl. No.: 16/266,654

(22) Filed: Feb. 4, 2019

(65) Prior Publication Data

US 2019/0183417 A1 Jun. 20, 2019

Related U.S. Application Data

(63) Continuation of application No. 15/116,277, filed as application No. PCT/IB2015/050632 on Jan. 28, 2015, now Pat. No. 10,194,857.

(Continued)

(51) Int. Cl.
*A61B 5/08* (2006.01)
*A61B 5/00* (2006.01)
(Continued)

(52) U.S. Cl.
CPC ............ *A61B 5/4836* (2013.01); *A61B 5/087* (2013.01); *A61B 5/0816* (2013.01);
(Continued)

(58) Field of Classification Search
CPC ............ A61M 16/024; A61M 16/0057; A61M 16/0465; A61M 16/0666; A61M 16/1075;
(Continued)

(56) References Cited

U.S. PATENT DOCUMENTS 5,535,738 A 7/1996 Estes
6,622,726 B1 9/2003 Du
(Continued)

FOREIGN PATENT DOCUMENTS

CN 103040468 A 4/2013
WO 2010076704 A1 7/2010
(Continued)

OTHER PUBLICATIONS

Owens et al, "Upper Airway Collapsibility and Patterns of Flow Limitation at Constant End-Expiratory Lung Volume", Journal of Applied Physiol., vol. 113, 2012, pp. 691-699.
(Continued)

*Primary Examiner* — Andrey Shostak

(57) ABSTRACT

Systems and methods for classifying breathing disorders of subjects are based on the respiratory response to a change in a pressure level of a pressurized flow of breathable gas. The change presents a breathing challenge to a subject. The challenge may be limited to the inspiratory breathing phase. The inspiratory pressure level may be lower than the expiratory pressure level during challenges.

12 Claims, 3 Drawing Sheets

Related U.S. Application Data

(60) Provisional application No. 61/941,631, filed on Feb. 19, 2014.

(51) Int. Cl.

| | |
|---|---|
| ***A61M 16/00*** | (2006.01) |
| ***A61M 16/16*** | (2006.01) |
| ***A61B 5/087*** | (2006.01) |
| ***A61M 16/04*** | (2006.01) |
| ***A61M 16/06*** | (2006.01) |
| ***A61M 16/10*** | (2006.01) |
| *A61M 16/20* | (2006.01) |

(52) U.S. Cl.

CPC .......... *A61B 5/4818* (2013.01); *A61B 5/7264* (2013.01); *A61B 5/7278* (2013.01); *A61M 16/0057* (2013.01); *A61M 16/0066* (2013.01); *A61M 16/024* (2017.08); *A61M 16/0465* (2013.01); *A61M 16/0666* (2013.01); *A61M 16/1075* (2013.01); *A61M 16/16* (2013.01); *A61B 5/082* (2013.01); *A61M 16/109* (2014.02); *A61M 16/161* (2014.02); *A61M 16/201* (2014.02); *A61M 2016/0036* (2013.01); *A61M 2205/3358* (2013.01); *A61M 2205/3375* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2230/40* (2013.01); *A61M 2230/50* (2013.01); *A61M 2230/63* (2013.01)

(58) Field of Classification Search

CPC .............. A61M 16/0066; A61M 16/16; A61M 2230/40; A61M 2016/0036; A61M 2205/3358; A61M 2205/3375; A61M 2205/50; A61M 2205/505; A61M 2205/52; A61M 2205/581; A61M 2205/583; A61M 2230/50; A61M 2230/63; A61M 16/109; A61M 16/161; A61M 16/201; A61B 5/4836; A61B 5/0816; A61B 5/087; A61B 5/4818; A61B 5/7264; A61B 5/7278; A61B 5/082

See application file for complete search history.

(56) References Cited

U.S. PATENT DOCUMENTS

| | | | | | |
|---|---|---|---|---|---|
| 7,081,095 | B2 * | 7/2006 | Lynn ...................... | A61B 5/087 128/203.23 |
| 2003/0055346 | A1 * | 3/2003 | Rapoport ............ | A61M 16/026 600/489 |
| 2006/0249149 | A1 * | 11/2006 | Meier ................. | A61M 16/024 128/204.18 |
| 2009/0082639 | A1 * | 3/2009 | Pittman ................ | A61B 5/4818 600/300 |
| 2009/0229611 | A1 | 9/2009 | Martin et al. | |
| 2011/0092839 | A1 | 4/2011 | Alshaer et al. | |
| 2011/0178968 | A1 | 7/2011 | Orr | |
| 2011/0240025 | A1 * | 10/2011 | Mechlenburg ...... | A61M 16/026 128/204.21 |
| 2011/0297156 | A1 | 12/2011 | Shelly et al. | |
| 2012/0227742 | A1 | 9/2012 | Witt et al. | |
| 2013/0199532 | A1 | 8/2013 | Shissler et al. | |

FOREIGN PATENT DOCUMENTS

| | | | |
|---|---|---|---|
| WO | 2010076711 | A1 | 7/2010 |
| WO | 2010076712 | A1 | 7/2010 |
| WO | 2010076713 | A1 | 7/2010 |
| WO | 2012001621 | A1 | 1/2012 |
| WO | 2013005201 | A1 | 1/2013 |

OTHER PUBLICATIONS

Wellman et al, "A Simplified Method for Determining Phenotypic Traits in Patients With Obstructive Sleep Apnea", Journal of Applied Physiol., vol. 114, 2013, pp. 911-922.

Eckert et al, "Variability in the Pathophysiological Phenotypic Causes of Obstructive Sleep Apnea: Targets for Novel Therapeutic Approaches", American Academy of Sleep Medicine, vol. 34, 2011, p. A159.

Eckert et al, "Defining Phenotypic Causes of Obstructive Sleep Apnea: Identification of Novel Therapeutic Targets", AJRCCM, 2013, pp. 1-30.

* cited by examiner

REVERSE DUAL POSITIVE AIRWAY PRESSURE CHALLENGES FOR BREATHING DISORDER DIAGNOSTICS

CROSS-REFERENCE TO PRIOR APPLICATIONS

This application is a Continuation application of U.S. National Phase application under 35 U.S.C. § 371, Ser. No. 15/116,277, filed on Aug. 3, 2016, which claims the benefit of International Application Serial No. PCT/IB2015/050632, filed on Jan. 28, 2015, which claims the benefit of U.S. Application Ser. No. 61/941,631, filed on Feb. 19, 2014. These applications are hereby incorporated by reference herein.

BACKGROUND

1. Field

The present disclosure pertains to systems and methods for classifying breathing disorders of subjects. In particular, the present disclosure pertains to adjusting the pressure level of a pressurized flow of breathable gas and determining a classification based on the respiratory response by a subject.

2. Description of the Related Art

Some types of respiratory therapy involve the delivery of a pressurized flow of breathable gas to the airway of a subject. A therapy session may (be intended to) span eight or more hours, and may (be intended to) coincide and/or overlap, at least in part, with a subject's daily and/or nightly sleeping period. A subject's comfort during a therapy session is a useful factor in therapy adoption rates and/or therapy success rates.

SUMMARY

Accordingly, one or more embodiments of the present disclosure provide a system that includes a pressure generator, one or more sensors, and one or more physical processors. The pressure generator is configured to provide a pressurized flow of breathable gas at a pressure level to an airway of a subject. The one or more sensors are configured to generate output signals conveying information related to breathing of the subject. The one or more physical processors configured to obtain a recommended respiratory therapy regimen for the subject that includes a recommended inspiratory positive airway pressure level and a recommended expiratory positive airway pressure level; determine one or more timing parameters related to the breathing of the subject based on the generated output signals; control the pressurized flow in accordance with the recommended respiratory therapy regimen such that the pressure level of the pressurized flow corresponds to the recommended inspiratory positive airway pressure (IPAP) level during inspirations and the pressure level of the pressurized flow corresponds to the recommended expiratory positive airway pressure (EPAP) level during expirations, wherein control is based on the one or more timing parameters; reduce the pressure level of the pressurized flow with respect to the recommended IPAP level during inspiration for one or more breathing cycles; determine one or more breathing parameters of the subject based on the generated output signals during the one or more breathing cycles; and determine a classification of a breathing disorder of the subject based on the determined one or more breathing parameters during the one or more breathing cycles. In some embodiments, the pressure levels during inspiration and expiration may be adjusted upward and/or downward independently of each other.

It is yet another aspect of one or more embodiments of the present disclosure to provide a method to classify a breathing disorder of a subject. The method is implemented using a pressure generator, one or more sensors, and one or more physical processors. The method includes providing a pressurized flow of breathable gas at a pressure level to an airway of the subject; generating output signals conveying information related to breathing of the subject; obtaining a recommended respiratory therapy regimen for the subject that includes a recommended inspiratory positive airway pressure (IPAP) level and a recommended expiratory positive airway pressure (EPAP) level; determining one or more timing parameters related to the breathing of the subject based on the generated output signals; controlling the pressurized flow of breathable gas in accordance with the recommended respiratory therapy regimen such that the pressure level of the pressurized flow corresponds to the recommended IPAP level during inspirations and the pressure level of the pressurized flow corresponds to the recommended EPAP level during expirations, wherein control is based on the one or more timing parameters; reducing the pressure level of the pressurized flow with respect to the recommended IPAP level during inspiration for one or more breathing cycles; determining one or more breathing parameters of the subject based on the generated output signals during the one or more breathing cycles; and determining a classification of a breathing disorder of the subject based on the determined one or more breathing parameters during the one or more breathing cycles.

It is yet another aspect of one or more embodiments to provide a system configured to classify a breathing disorder of a subject. The system includes means for providing a pressurized flow of breathable gas at a pressure level to an airway of the subject; means for generating output signals conveying information related to breathing of the subject; means for obtaining a recommended respiratory therapy regimen for the subject that includes a recommended inspiratory positive airway pressure level and a recommended expiratory positive airway pressure level; means for determining one or more timing parameters related to the breathing of the subject based on the generated output signals; means for controlling the pressurized flow of breathable gas in accordance with the recommended respiratory therapy regimen such that the pressure level of the pressurized flow corresponds to the recommended IPAP level during inspirations and the pressure level of the pressurized flow corresponds to the recommended EPAP level during expirations, wherein operation of the means for controlling is based on the one or more timing parameters; means for reducing the pressure level of the pressurized flow with respect to the recommended IPAP level during inspiration for one or more breathing cycles; means for determining one or more breathing parameters of the subject based on the generated output signals during the one or more breathing cycle; and means for determining a classification of a breathing disorder of the subject based on the determined one or more breathing parameters during the one or more breathing cycles.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
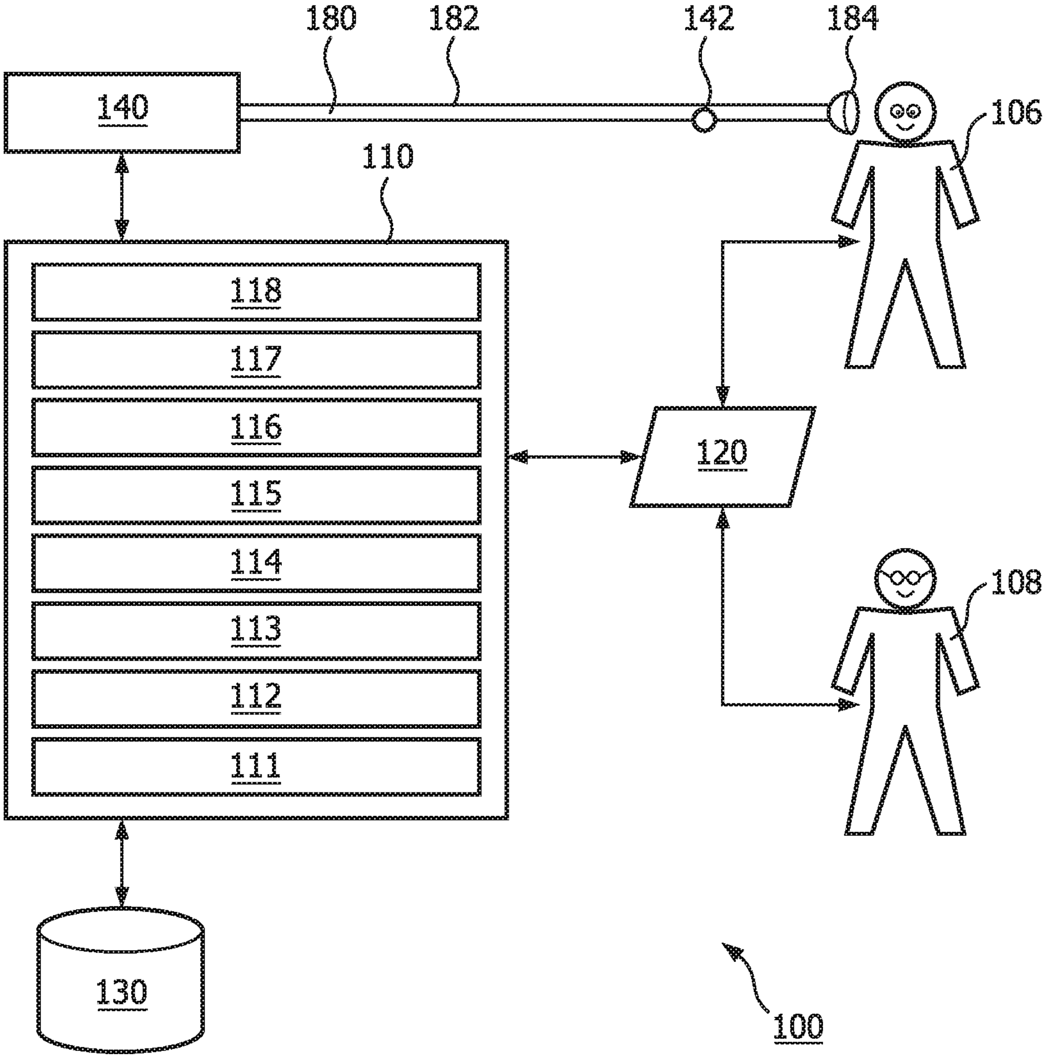
FIG. 1 schematically illustrates a system to classify breathing disorders, according to certain embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A subject's comfort during a therapy session may be a useful and/or important factor in therapy adoption rates and/or therapy success rates. Due to poor comfort, many subjects do not like (CPAP) therapy. For example, approximately 50% of subjects quit using CPAP therapy within several months. It is generally held that 50% of the affected population does not choose to seek medical care for Sleep Disorder Breathing (SDB) in the first place, with one of the main reasons being that the CPAP is considered an unacceptable treatment. There are a growing number of alternative treatments that are viewed more favorably by the under-served, but the issue is that virtually all of those alternatives only treat specific segments of the patient population, due to the fact that these alternatives treat only specific causes of obstruction or airway instability. These alternatives may be successful responsive to a given subject having success with treating their particular SBD root cause, in addition to the general use of the intervention being acceptable to them. By virtue of this disclosure, subjects may be increasingly confident in knowing that the treatment will work in a particular case, since the particular root cause may be determine and/or classified. Once a root cause has been determined and/or classified, more viable options may be provided to a subject that are customized for the individual subject's problems and preferences.

FIG. 1 schematically illustrates a system 100 configured to classify breathing disorders for subjects, for example a subject 106 having an airway. Classification of breathing disorders, in particular by the source or (root) cause of a disorder, may enable selection of a proper intervention and/or treatment. Classifying subjects or patients (based on the type of breathing disorder) may be referred to as phenotyping patients. A subject's phenotype may determine (and/or be used to determine) the interventions and type of care most likely and/or best suited to treat their condition or disease.

System 100 may be implemented as, integrated with, and/or operating in conjunction with a respiratory device that provides a pressurized flow of breathable gas along a flow path to subject 106. System 100 may include one or more of a pressure generator 140, a subject interface 180, one or more sensors 142, an electronic storage 130, a user interface 120, a processor 110, a therapy component 111, a timing component 112, a control component 113, a challenge component 114, a breathing parameter component 115, a classification component 116, a relief component 117, a stability component 118, and/or other components. System 100 may be configured to provide respiratory therapy to subject 106.

Pressure generator 140 of system 100 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via one or more subject interfaces 180. Subject interface 180 may sometimes be referred to as a delivery circuit.

As depicted in FIG. 1, pressure generator 140 fluidly communicates with subject interface 180. Subject interface 180 fluidly communicates, via a subject interface appliance 184, with the airway of subject 106. The configuration of various components in FIG. 1 is not intended to limit the scope of the described technology in any way. For example, in some embodiments, system 100 may include a humidifier and/or interface heating system disposed between pressure generator 140 and subject 106.

Respiratory therapy may be implemented as pressure control, pressure support, volume control, and/or other types of support and/or control. For example, to support inspiration, the pressure of the pressurized flow of breathable gas may be adjusted to an inspiratory positive airway pressure (interchangeably referred to as inspiratory pressure, IPAP, or IPAP level). Alternatively, and/or simultaneously, to support expiration, the pressure and/or flow of the pressurized flow of breathable gas may be adjusted to an expiratory positive airway pressure (interchangeably referred to as expiratory pressure, EPAP, or EPAP level). Other schemes for providing respiratory support and/or ventilation through the delivery of the pressurized flow of breathable gas are contemplated. Subject 106 may but need not initiate one or more phases of respiration. Devices that provide different IPAP and EPAP levels may be referred to as dual (positive) airway pressure devices. An example of a dual positive airway pressure device is a BiPAP® device. Typically for dual positive airway pressure devices, the IPAP level is higher than the EPAP level. As used herein, providing a lower IPAP level than EPAP level may be referred to as reverse dual positive airway pressure, since it is the opposite of typical dual positive airway pressure.

System 100 may be configured to adjust and/or maintain levels of pressure, flow, humidity, velocity, acceleration, and/or other parameters of the humidified, pressurized flow of breathable gas. One or more adjustments may occur in substantial synchronization with the breathing cycle of the subject. In some embodiments, one or more operating levels (e.g. pressure, volume, etc.) are adjusted on a relatively ongoing manner (e.g., each breath, every few breaths, every few seconds, etc.) during an individual session of respiratory therapy to titrate the therapy. Alternatively, and/or simultaneously, adjustments to one or more operating levels of system 100 and/or any component thereof may be made more intermittently and/or between therapy sessions rather than during a particular therapy session.

Pressure generator 140 is configured to provide and/or deliver a pressurized flow of breathable gas to the airway of subject 106, e.g. via one or more subject interfaces 180. Subject interface 180 may include a conduit 182 and/or a subject interface appliance 184. As depicted in FIG. 1, subject interface 180 may include a conduit 182. Conduit 182 may include a flexible length of hose, or other conduit. As depicted in FIG. 1, conduit 182 may place subject interface appliance 184 in fluid communication with pressure generator 140. Conduit 182 may form a flow path through which the pressurized flow of breathable gas is communicated between subject interface appliance 184 and pressure generator 140.

Subject interface appliance 184 of system 100 in FIG. 1 is configured to deliver the pressurized flow of breathable gas to subject 106, e.g. to the airway of subject 106. Subject interface appliance 184 may be configured to reduce and/or inhibit condensation from forming along the path of delivery of a pressurized flow of breathable gas to subject 106. Subject interface appliance 184 may include any appliance suitable for the described function.

In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Subject interface appliance 184 may be configured to be removably coupled to conduit 182. Subject interface appliance 184 may be configured to be installed in the face of subject 106 to place the airway of subject 106 in fluid communication with conduit 182 for delivery of a pressurized flow of breathable gas through conduit 182 to the airway of subject 106.

Electronic storage 130 of system 100 in FIG. 1 comprises physical electronic storage media that electronically stores information, e.g. digital information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., a user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing operational settings of pressure generator 140 as selected and/or preferred by subject 106. An example of information that user 108 or subject 106 may provide to system 100 is a target temperature or target pressure level during respiratory therapy. Examples of interface devices suitable for inclusion in user interface 120 include a keypad, buttons, switches, a keyboard, knobs, dials, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the embodiment of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying information related to the breathing of subject 106 and/or to physiological parameters of subject 106, including but not limited to respiratory parameters. One or more sensors 142 may be in fluid communication with conduit 182, subject interface appliance 184, and/or other components of system 100. In some embodiments, the generated output signals may convey measurements related to parameters of the flow of breathable gas within system 100. By way of non-limiting example, the parameters may include respiratory parameters, timing parameters, physiological parameters, environmental parameters, medical parameters, and/or other parameters.

The parameters may include one or more of (peak) flow, flow rate, volume, leak flow, leak volume, (airway) pressure, barometric pressure, temperature, humidity, velocity, acceleration, and/or other parameters. The respiratory parameters may include respiratory timing parameters, including but not limited to parameters related to transitions in breathing between inhalations/inspirations and exhalations/expirations, transition time from peak inhalation flow rate to peak exhalation flow rate and/or vice versa, transitions moments or durations, breathing period, respiratory rate, inspiration time or period, expiration time or period, start and/or end in inspiratory phases, start and/or end of expiratory phases, and/or other respiratory timing parameters.

Environmental parameters may be related to one or more of the parameters of electromagnetic radiation, various temperatures, humidity levels, and/or other environmental parameters, which may be related to environmental conditions near system 10 or near subject 106. One or more medical parameters may be related to monitored vital signs of subject 106, physiological parameters of subject 106, and/or other medical parameters of subject 106.

One or more sensors 142 may generate output signals conveying information related to parameters associated with the state and/or condition of an airway of subject 106, the breathing of subject 106, the breathing rate of subject 106, the gas delivered to subject 106, the composition, temperature, and/or humidity of the gas delivered to subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 100. This transmission may be wired and/or wireless.

Physiological parameters may be related to patient movement, cardio-vascular function, pulmonary function, central nervous system function, local motor-neuron function, mechanical motion of the body or its organs, and/or other parameters. In some embodiments, sensor 142 may include sensors to monitor subject 106, including, but not limited to, sensors to measure polysomnography, electro-encephalography (EEG), electro-oculography (EOG), electromyography (EMG), electrocardiography (ECG), and/or sensors for other types of monitoring.

The illustration of sensor 142 including one member in FIG. 1 is not intended to be limiting. The illustration of a sensor 142 at or near subject interface appliance 184 is not intended to be limiting, though that location may be preferred in some embodiments to provide feedback and/or information regarding the current flow rate of the pressurized flow of breathable gas being delivered to the airway of subject 106. For example, this current flow rate may function as feedback for a target flow rate for controlling pressure generator 140.

Processor 110 of system 100 in FIG. 1 is configured to provide information processing capabilities in system 100. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program components. The one or more computer program components include one or more of therapy component 111, timing component 112, control component 113, challenge component 114, breathing parameter component 115, classification component 116, relief component 117, stability component 118, and/or other components. Processor 110 may be configured to execute components 111-118 by software; hardware; firmware; some combination of software, hardware, and/or firmware; and/or other mechanisms for configuring processing capabilities on processor 110.

It should be appreciated that although components 111-118 are illustrated in FIG. 1 as being co-located within a single processing unit, in embodiments in which processor 110 includes multiple processing units, one or more of components 111-118 may be located remotely from the other components. The description of the functionality provided by the different components 111-118 described herein is for illustrative purposes, and is not intended to be limiting, as any of components 111-118 may provide more or less functionality than is described. For example, one or more of components 111-118 may be eliminated, and some or all of its functionality may be provided by other ones of components 111-118. Note that processor 110 may be configured to execute one or more additional components that may perform some or all of the functionality attributed below to one of components 111-118. In some embodiments, some or all of the described functionality of an individual computer program component may be incorporated, shared, embedded, and/or integrated into one or more other computer program components or elsewhere within system 100.

Therapy component 111 may be configured to obtain a respiratory therapy regimen for subject 106. For example, the obtained respiratory therapy regimen may be a recommended respiratory therapy regimen. In some embodiments, therapy component 111 may be configured to obtain a respiratory therapy regimen from a user (such as subject 106 and/or user 108, a caregiver, a therapy decision-maker, etc.). In some embodiments, therapy component 111 may be configured to obtain and/or receive a respiratory therapy regimen that may be determined and/or devised algorithmically based on, at least, subject-specific information. In some embodiments, therapy component 111 may be configured to determine a recommended respiratory therapy regimen, e.g. based on, at least, subject-specific information. Additional information that may be used to determine a respiratory therapy regimen may be obtained from and/or through a knowledge base (or knowledge database).

In some embodiments, the obtained respiratory therapy regimen may include a recommended inspiratory positive airway pressure (IPAP) level, a recommended expiratory positive airway pressure (EPAP) level, and/or other recommended pressure levels. In some embodiments, the recommended pressure levels may be determined and/or selected to maintain breathing by subject 106 that is free of apneas, hypopneas, and/or other respiratory events, or at least expected to be so. In some embodiments, the recommended pressure levels may be determined and/or selected such that the airway of subject 106 is deemed and/or expected to be stable and/or unobstructed. In some embodiments, the recommended pressure levels may be selected to be below a prescribed continuous positive airway pressure (CPAP) level to treat apnea and/or other respiratory events. Determinations and/or selections by therapy component 111 may be based on determinations by other computer program components, including but not limited to stability component 118.

Timing component 112 may be configured to determine one or more timing parameters related to the breathing of subject 106, including but not limited to respiratory timing parameters described elsewhere in this disclosure. For example, timing parameters may include the moment of onset of inspiration, the moment of onset of expiration, (estimated or measured) duration or period of inspiration, (estimated or measured) duration or period of expiration, pause between inspiration and expiration and/or vice versa, transition time from peak inhalation flow rate to peak exhalation flow rate and/or vice versa, start and/or end in inspiratory phases, start and/or end of expiratory phases, and/or other respiratory timing parameters, combinations of respiratory timing parameters, and/or parameters based thereon.

Control component 113 may be configured to control operation of system 100, pressure generator 140, and/or related components. Control component 113 may be configured to perform control functionality in multiple modes of operation. Control component 113 may be configured to control transitions between different modes of operation. Control component 113 may be configured to determine what the current mode of operation is, and/or share such information with other components of system 100. Control component 113 may be configured to control pressure generator 140 such that one or more gas parameters of the pressurized flow of breathable gas are varied over time in accordance with a respiratory therapy regimen. Control component 113 may be configured to control pressure generator 140 to provide the pressurized flow of breathable gas at inhalation pressure levels (e.g. the recommended IPAP level) during inhalation phases, and at exhalation pressure levels (e.g. the recommended EPAP level) during exhalation phases. For example, a first mode may correspond to providing challenges to subject 106, as described elsewhere in this disclosure. A second mode of operation may correspond to providing relief to subject 106 after a particular obstruction or other respiratory event has occurred. Other modes of operation are envisioned within the scope of this disclosure.

Parameters determined by other computer program components and/or received through one or more sensors 142 may be used by control component 113, e.g. in a feedback manner, to adjust one or more therapy modes/settings/operations of system 100. Alternatively, and/or simultaneously, signals and/or information received through user interface 120 may be used by control component 113, e.g. in a feedback manner, to adjust one or more therapy modes/settings/operations of system 100. Control component 113 may be configured to time its operations relative to the transitional moments in the breathing cycle of a subject, over multiple breath cycles, and/or in any other relation to any detected occurrences or determinations by timing component 112.

Challenge component 114 may be configured to adjust one or more pressure levels of the pressurized flow of breathable gas being delivered to subject 106. In some embodiments, the provided pressure levels during inspiration and expiration may be adjusted upward and/or downward independently of each other. For example, challenge component 114 may be configured to reduce the inspiratory pressure level to be below the recommended IPAP level, for one or more breathing cycles. In some embodiments, the reduced inspiratory level may be lower than the recommended and/or actually provided expiratory pressure level. In some embodiments, a subject may be initially titrated to a particular CPAP level or two particular BiPAP levels that may enable the subject to breathe normally (i.e. in a eupneic state, or a state of being treated), for example as characterized by the subject's body exhibiting compensatory functions at a minimum level of activity, e.g. removing the body's need to overcome a challenge, obstruction, condition, and/or disease. A set of one or more breathing cycles for which the inspiratory pressure level is reduced may be referred to as a challenge, since the subject will need to compensate in response. The response to the adjustment, e.g. to the reduced IPAP level, may be indicative of a type of obstruction, and/or may be used as a basis for a classification by classification component 116. Subjects having different types of breathing disorders may respond differently to certain challenges. In some embodiments, the response may be indicative of the airway reactivity to changes in lung volume and/or airway pressure. By virtue of separate and individual pressure control for the respiratory phases, interaction between the respiratory phases may be assessed.

In some embodiments, challenge component 114 may be configured to provide a set of challenges, e.g. such that subsequent challenges have different levels of inspiratory pressure levels. In some embodiments, the inspiratory pressure level may be repeatedly reduced through subsequent challenges until a particular condition occurs. The particular condition may include a timing parameter and/or breathing parameter breaching a particular threshold. In some embodiments, the particular condition may be a determination that the stability of the airway has been compromised, e.g. through an obstruction, an arousal, a type of apnea, hypopnea, or other respiratory event, a type of sleep disordered breathing (SDB), etc. In some embodiments, the particular condition may be a determination that indicates airway instability. As used herein, an onset of airway instability may be considered an indication of airway instability. Alternatively, and/or simultaneously, a determination that the stability of the airway has been compromised may be considered an indication of airway instability. The particular challenge at which the particular condition occurs may be referred to as a point of interest for diagnostic purposes. For example, the IPAP level may be reduced gradually until some type of respiratory event (or obstruction in the airway of subject 106) occurs. The amount of reduced pressure needed to accomplish a particular occurrence may be used as a parameter by other computer program components, including but not limited to classification component 116. The IPAP level may be reduced temporarily, during challenges, to a pressure level below traditional treatment levels. For example, the reduced IPAP pressure level may be about 1 cm-$H_2O$, about 2 cm-$H_2O$, about 3 cm-$H_2O$, about 4 cm-$H_2O$, about 5 cm-$H_2O$, about 6 cm-$H_2O$, and/or another suitable pressure level.

In some embodiments, challenge component 114 may be configured to provide one or more challenges with respect to a point of interest. For example, challenge component 114 may be configured to reduce the EPAP level at such a point in order to determine (one or more parameters indicative of) how subject 106 responds. For example, the response may indicate a sensitivity of subject 106 to adjustments at or near a particular point of interest. In some embodiments, the response by subject 106 to a reduced EPAP level (in addition to a reduced IPAP level) may indicate severe airway instability (e.g. limited or no flow being measured). The particular EPAP adjustment that corresponds to such an indication may be referred to as a point of interest for diagnostic purposes. At various points of interest, adjustments to the inspiratory pressure and/or expiratory pressure may be made, in order to determine a response by subject 106. Responses by subject 106 to one or more pressure adjustments, in particular at or near points of interest, may be used as a basis for a classification by classification component 116.

Breathing parameter component 115 may be configured to determine one or more breathing parameters of subject 106, e.g. for the one or more breathing cycles that correspond to a challenge. Determinations by breathing component 115 may be based on output signals generated by one or more sensors 142 and/or determinations by other computer program modules. As used herein, breathing parameters may include gas parameters.

By way of non-limiting example, breathing parameters may include one or more of (peak) flow, flow rate, leak flow, leak correction volume, (estimated) flow limitation during exhalation, residual volume, maximum inspiratory flow per breath, (tidal) volume, minute volume, inhalation or exhalation pressures, respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), change in pressure during the first 0.1 s of an inspiration, change in flow rate during the last 0.1 s of an exhalation, (estimated) airway resistance, (estimated) airway compliance, gas temperature, gas humidity, gas velocity, gas acceleration, gas composition (e.g. concentration(s) of one or more constituents such as, e.g., $CO_2$), thermal energy dissipated, (intentional) gas leak, and/or other measurements related to the (pressurized) flow of breathable gas and/or other breathing parameters. In some embodiments, a breathing parameter may include ratios and/or other combinations of multiple other parameters. Some or all of this functionality may be incorporated, shared, and/or integrated into other computer program components in system 100.

By way of non-limiting example, the one or more breathing parameters may include a delay parameter that indicates a delay between an onset of an inspiratory phase that has a reduced pressure level and a change in inspiratory flow rate that corresponds to the onset of the inspiratory phase. In some embodiments, the delay parameter may have a different value for different types of challenges, depending on the type of obstruction and/or breathing disorder. The delay parameter may be indicative of a particular type of obstruction and/or breathing disorder. In some embodiments, the delay parameter may change between different challenges, which may be indicative of a particular type of obstruction and/or breathing disorder. In some embodiments, the delay parameter may be substantially constant between different challenges, which may be indicative of another particular type of obstruction and/or breathing disorder. In some embodiments, the delay parameter may be used as a basis for a classification by classification component 116.

Classification component 116 may be configured to determine classifications of breathing disorders of subjects. In some embodiments, a classification may pertain to a type of apnea, hypopnea, or other respiratory event. In some embodiments, a classification may pertain to a physical cause or a chemical cause, such as a particular chemical balance in the blood of subject 106. In some embodiments, a classification may pertain to a type of sleep disordered breathing (SDB), including but not limited to snoring, upper airway resistance syndrome (UARS), obstructive sleep apnea (OSA), and/or other types of sleep disordered breathing. In some embodiments, a classification may pertain to different types of snoring, i.e. types of snoring caused by or at different sites of a subject. For example, a classification may pertain to obstructions located at different sites and/or caused by different types of soft tissue, including but not limited to tongue, epiglottis, palate, esophageal flap, throat walls, airway walls, pharyngeal walls, and/or other bulk tissue or soft tissue. For example, a classification may distinguish between two or more different types of obstructions. As used herein, the term obstruction may be interpreted to include collapses.

In some embodiments, determinations by classification component 116 may be based on one or more determinations by breathing parameter component 115, in particular for the one or more breathing cycles corresponding to a particular challenge. In some embodiments, a first determination by breathing parameter component 115 for the first breathing cycle of a particular challenge may be compared with a second determination by breathing parameter component 115 for the second breathing cycle of the particular challenge, and so forth.

In some embodiments, determinations by classification component 116 may be based on one or more determinations by breathing parameter component 115, in particular by comparing determinations for the one or more breathing cycles corresponding to a first challenge with determination for the one or more breathing cycles corresponding to a second and/or third challenge, and so forth. The classification component 116 may also use inputs from other systems, the subject's answers to questions, measured parameters, and/or ethnographic parameters in order to make determinations by classification component 116 more comprehensive, accurate, or precise.

Stability component 118 may be configured to determine whether the airway of subject 106 is stable and/or whether one or more parameters indicate airway instability. In some embodiments, stability component 118 may be configured to determine whether (an onset of) an obstruction, a type of apnea, hypopnea, or other respiratory event, or a type of sleep disordered breathing has occurred. For example, an onset of an arousal may be deemed to indicate airway instability. Alternatively, and/or simultaneously, stability component 118 may be configured to determine whether stability of the airway has been restored, or whether an obstruction, a type of apnea, hypopnea, or other respiratory event, or a type of sleep disordered breathing has been removed, reverted, and/or ceased. For example, a change in the one or more parameters that previously indicated airway instability may indicate that the airway instability has been remedied. For example, the body of subject 106 may react to airway instability through an arousal, an onset of an arousal, a precursor to an arousal, and/or other physical reactions that may lead to an arousal.

Relief component 117 may be configured to adjust one or more pressure levels of the provided pressurized flow of breathable gas, in particular in an attempt to restore stability of the airway of subject 106. For example, relief component 117 may be configured to increase the EPAP level and/or IPAP level responsive to a particular determination or condition, including but not limited to stability of the airway of subject 106 having been compromised, and/or airway instability being indicated by one or more parameters. The response to the adjustment, e.g. to an increased EPAP level, may be indicative of a type of obstruction, and/or may be used as a basis for a classification by classification component 116. Relief component 117 may be configured to repeatedly make adjustments, e.g. increase the EPAP level, until, e.g., stability of the airway of subject 106 has been restored and/or airway instability is no longer indicated by the one or more parameters. The particular combination of inspiratory and expiratory levels at which the particular condition occurs, e.g. onset of airway instability, may be referred to as a point of interest for diagnostic purposes. The amount of adjusted pressure needed to accomplish this may be used as a parameter by other computer program components, including but not limited to classification component 116. For example, the amount of increased EPAP pressure needed to resolve snoring may be different (e.g. typically lower) than the amount of increased EPAP pressure needed to prevent apneas (e.g. typically higher). Either amount of pressure may correspond to a separate point of interest, and either point of interest may be used as a parameter by other computer program components, including but not limited to classification component 116.

At various points of interest, adjustments to the inspiratory pressure and/or expiratory pressure may be made, in order to determine a response by subject 106. For example, at a point of severe airway instability, relief component 117 may be configured to increase the IPAP level to provide relief. Responses by subject 106 to one or more pressure adjustments, in particular at or near points of interest, may be used as a basis for a classification by classification component 116.

Figure 3:
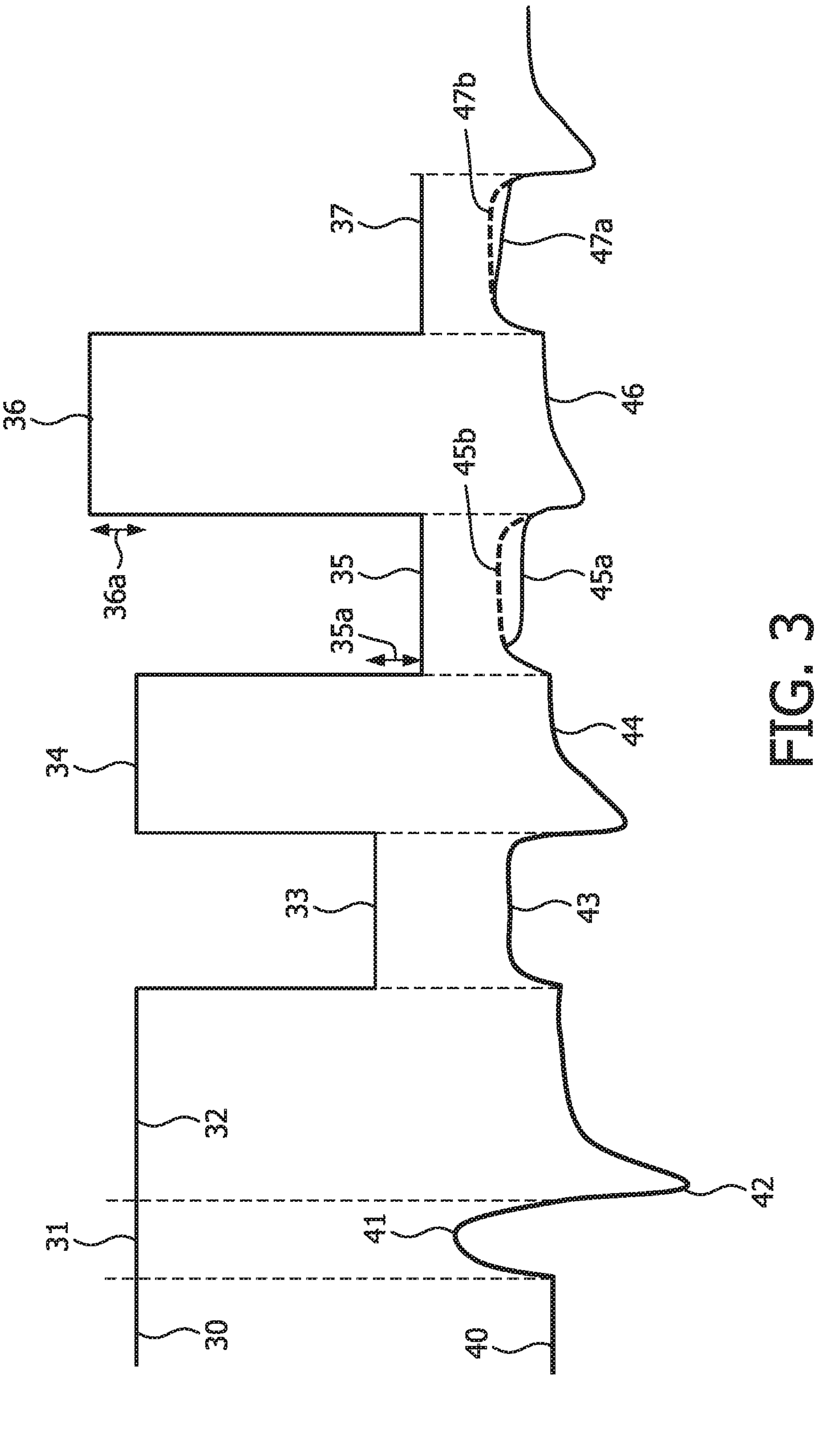
FIG. 3 illustrates a varying pressure level of a pressurized flow of breathable gas provided to a subject and further illustrates a corresponding flow rate of the subject that may be used to classify a breathing disorder according to certain embodiments.

By way of illustration, FIG. 3 illustrates a varying pressure level 30 of a pressurized flow of breathable gas provided to a subject and further illustrates a corresponding flow rate 40 of the subject that may be used to classify a breathing disorder. Periods 31, 33, 35, and 37 correspond to inspirations or inspiration phases of breathing cycles. Periods 32, 34, and 36 corresponds to expirations or expiration phases of breathing cycles. As depicted, the pressure levels during period 31 and period 32 may be the same. The corresponding patient flow 41-42 for the 31-32 periods show stable eupneic breathing. The combination of a period and the corresponding patient flow may be referred to as a segment, for example segment 31/41. Inspiratory flow rate 41, 43, 45*a*, and 47*a* correspond to periods 31, 33, 35, and 37, respectively. Expiratory flow rate 42, 44, and 46 correspond to period 32, 34, and 36, respectively. Period 33 corresponds to a first challenge for the subject, in this case a reduced inspiratory pressure level, as depicted by the difference in pressure level between the pressure level in period 31 and period 33. Period 33 and period 34 form a breathing cycle. Note that the expiratory pressure level in period 34 is the same as in period 32. The first challenge as depicted spans one breathing cycle, but this is merely exemplary. One or more characteristics of inspiratory flow rate 43 (e.g. in comparison with inspiratory flow rate 41) may be used to determine a classification as described elsewhere herein. In this example, the patient's airway is exhibiting some level of flow limitation (i.e. flattening and broadening of the waveform in period 33, when compared to the waveform in period 31), because they are no longer experiencing treatment pressure during inhalation on this breath, and something about their anatomy fails to keep the airway completely open.

Period 35 corresponds to a second challenge for the subject, in this case an even more reduced inspiratory pressure level compared to period 33, as depicted by a difference 35*a* in pressure level between period 33 and period 35. The second challenge as depicted spans one breathing cycle, but this is merely exemplary. Inspiratory flow rate 45*a* indicates the measured inspiratory flow rate that corresponds to inspiratory period 35. Expected inspiratory flow rate 45*b* corresponds to the inspiratory flow rate as expected for a stable airway of the subject. The difference between measured inspiratory flow rate 45*a* and expected inspiratory flow rate 45*b* may indicate that the stability of the airway of the subject may have been compromised. One or more characteristics of this difference may be used to determine a classification as described elsewhere herein. For example, the difference may correspond to a lower-than-expected pressure induced volume. In other words, the second challenge was too great to maintain a stable airway. To relieve the subject, the expiratory pressure during period 36 may be increased compared to period 34, as indicated by a difference 36*a*. Inspiratory flow rate 47*a* indicates the measured inspiratory flow rate that corresponds to inspiratory period 37. Expected inspiratory flow rate 47*b* corresponds to the inspiratory flow rate as expected for a more stable airway of the subject; for instance in the 33/43 segment. The difference between measured inspiratory flow rate 47*a* and expected inspiratory flow rate 47*b* may indicate that the stability of the airway of the subject continues to be compromised to some degree, but appears to have improved since the amplitude of flow is higher than during segment 35/45, and the difference between measured inspiratory flow rate 45*a* and expected inspiratory flow rate 45*b* is greater than the difference between measured inspiratory flow 47*a* and expected inspiratory flow rate 47*b*. One or more characteristics of this difference may be used to determine a classification as described elsewhere herein. Note the different shape of measured inspiratory flow 47*a* compared to the measured inspiratory flow 45*a*. Note that measured inspiratory flow 47*a* is higher than the measured inspiratory flow 45*a*. In other words, the attempt to provide relief for the subject has not yet (e.g. fully) succeeded to restore stability of the airway of the subject. For example, perhaps an additional increase of the expiratory pressure level would restore the stability. The response of the inspiratory pressure level to various adjustments of inspiratory and/or expiratory pressure levels may indicate, for example in combination, a particular classification of a breathing disorder. Note that characteristics of differences between measured and expected flow rate are not limited to inspiratory phases, but may apply in a similar manner to expiratory phases.

Figure 2:
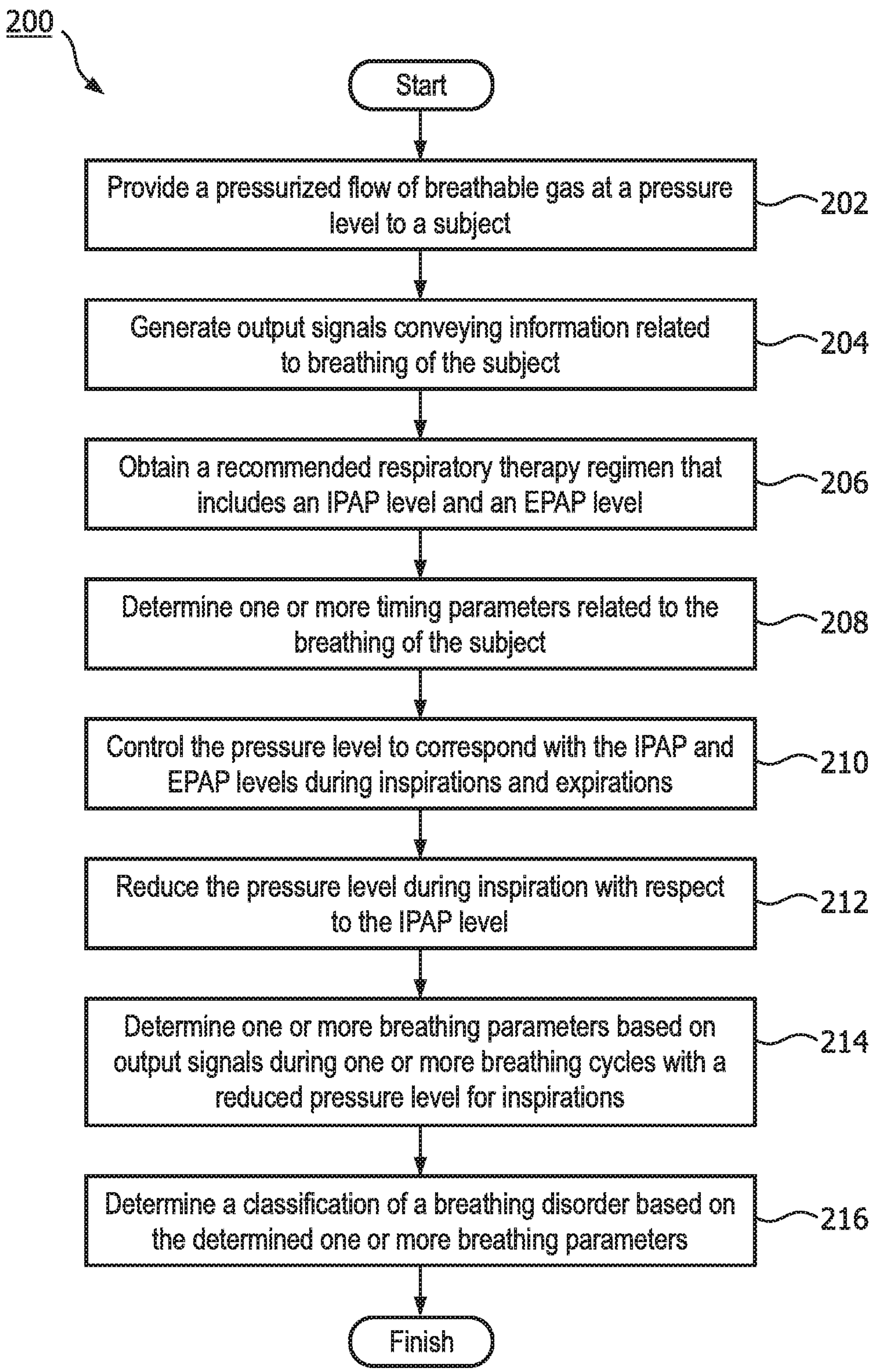
FIG. 2 illustrates a method to classify a breathing disorder of a subject, according to certain embodiments.

FIG. 2 illustrates a method 200 to classify a breathing disorder of a subject. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is provided at a pressure level to an airway of the subject. In some embodiments, operation 202 is performed by a pressure generator the same as or similar to pressure generator 140 (shown in FIG. 1 and described herein).

At an operation 204, output signals are generated conveying information related to breathing of the subject. In some embodiments, operation 204 is performed by one or more sensors the same as or similar to one or more sensors 142 (shown in FIG. 1 and described herein).

At an operation 206, a recommended respiratory therapy regimen is obtained for the subject that includes a recommended inspiratory positive airway pressure (IPAP) level and a recommended expiratory positive airway pressure (EPAP) level. In some embodiments, operation 206 is performed by a therapy component the same as or similar to therapy component 111 (shown in FIG. 1 and described herein).

At an operation 208, one or more timing parameters are determined related to the breathing of the subject based on the generated output signals. In some embodiments, operation 208 is performed by a timing component the same as or similar to timing component 112 (shown in FIG. 1 and described herein).

At an operation 210, the pressurized flow of breathable gas is controlled in accordance with the recommended respiratory therapy regimen such that the pressure level of the pressurized flow corresponds to the recommended IPAP level during inspirations and the pressure level of the pressurized flow corresponds to the recommended EPAP level during expirations. Control is based on the one or more timing parameters. In some embodiments, operation 210 is performed by a control component the same as or similar to control component 113 (shown in FIG. 1 and described herein).

At an operation 212, the pressure level of the pressurized flow is reduced with respect to the recommended IPAP level during inspiration for one or more breathing cycles. In some embodiments, operation 212 is performed by a challenge component the same as or similar to challenge component 114 (shown in FIG. 1 and described herein).

At an operation 214, one or more breathing parameters of the subject are determined based on the generated output signals during the one or more breathing cycles, and. In some embodiments, operation 214 is performed by a breathing parameter component the same as or similar to breathing parameter component 115 (shown in FIG. 1 and described herein).

At an operation 216, a classification of a breathing disorder of the subject is determined based on the determined one or more breathing parameters during the one or more breathing cycles. In some embodiments, operation 216 is performed by a classification component the same as or similar to classification component 116 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A pressure support system configured to provide pressure support to an airway of a subject, the system comprising:

a pressure generator configured to provide a pressurized flow of breathable gas at a pressure level to the airway of the subject;

a subject interface configured to conduct the pressurized flow of breathable gas to the airway of the subject, the subject interface including an interface appliance configured to removably engage the airway of the subject;

one or more sensors in fluid communication with the subject interface and configured to generate output signals conveying information related to breathing of the subject; and one or more physical processors configured to:

receive a recommended inspiratory positive airway pressure (IPAP) level and a recommended expiratory positive airway pressure (EPAP) level;

control the pressure generator based on the output signals to generate the pressurized flow such that the pressure level of the pressurized flow corresponds to the recommended IPAP level during inspirations of the subject and the pressure level of the pressurized flow corresponds to the recommended EPAP level during expirations of the subject;

control the pressure generator to repeatedly reduce the pressure level of the pressurized flow with respect to the recommended IPAP level during inspiration for one or more breathing cycles until the output signals indicate airway instability of the subject;

determine a reduction amount of the pressure level resulting from the repeated reduction that caused the airway instability based on the generated output signals during the one or more breathing cycles; and determine a classification of a breathing disorder of the subject based on the reduction amount of the pressure level that caused the airway instability.

2. The system of claim 1, wherein the one or more physical processors are configured such that the repeated reducing comprises:

reducing the pressure level during a first inspiration to a first reduced level and during a second inspiration to a second reduced level, wherein the second inspiration is subsequent to the first inspiration, determining a first breathing parameter during the first inspiration and a second breathing parameter during the second inspiration, and determining a difference between the first breathing parameter and the second breathing parameter, and wherein the classification is further based on the determined difference.

3. The system of claim 1, wherein the one or more physical processors are further configured to:

determine a first inspiratory flow rate during one or more inspirations that have the recommended IPAP level, determine a second inspiratory flow rate during the one or more breathing cycles with the reduced pressure level, and further determine the classification of the breathing disorder of the subject based on a change between the first inspiratory flow rate and the second inspiratory flow rate.

4. The system of claim 1, wherein the one or more physical processors are further configured to:

repeatedly increase the pressure level of the pressurized flow with respect to the recommended EPAP level during expirations for one or more breathing cycles; and determine whether stability of the airway has been restored based on the generated output signals, wherein the classification of the breathing disorder of the subject is further based on an amount the pressure level is increased during expirations to restore the stability of the airway.

5. A method for providing pressure support to an airway of a subject, the method being implemented using a pressure generator that provides a pressurized flow of breathable gas at a pressure level to the airway of the subject, a subject interface, one or more sensors in fluid communication with the subject interface, and one or more physical processors, the method comprising:

generating, with the pressure generator, the pressurized flow of breathable gas at the pressure level for delivery to the airway of the subject;

conducting, with the subject interface, the pressurized flow of breathable gas to the airway of the subject, the subject interface including an interface appliance configured to removably engage the airway of the subject;

generating, by the one or more sensors, output signals conveying information related to breathing of the subject;

receiving, with the one or more physical processors, a recommended inspiratory positive airway pressure (IPAP) level and a recommended expiratory positive airway pressure (EPAP) level;

controlling, with the one or more physical processors, the pressure generator based on the output signals to generate the pressurized flow of breathable gas such that the pressure level of the pressurized flow corresponds to the recommended IPAP level during inspirations of the subject and the pressure level of the pressurized flow corresponds to the recommended EPAP level during expirations of the subject;

repeatedly reducing, by controlling the pressure generator with the one or more physical processors, the pressure level of the pressurized flow with respect to the recommended IPAP level during inspiration for one or more breathing cycles until the output signals indicate airway instability of the subject;

determining, with the one or more physical processors, a reduction amount of the pressure level resulting from the repeated reduction; and determining, with the one or more physical processors, a classification of a breathing disorder of the subject based on the reduction amount of the pressure level that caused the airway instability.

6. The method of claim 5, wherein repeatedly reducing the pressure level includes:

reducing the pressure level during a first inspiration to a first reduced level;

reducing the pressure level during a second inspiration to a second reduced level, wherein the second inspiration is subsequent to the first inspiration, determining a first breathing parameter during the first inspiration;

determining a second breathing parameter during the second inspiration; and determining a difference between the first breathing parameter and the second breathing parameter;

and wherein determining the classification is further based on the difference between the first breathing parameter and the second breathing parameter.

7. The method of claim 5, further comprising:

determining, with the one or more physical processors, a first inspiratory flow rate during one or more inspirations that have the recommended IPAP level, determining, with the one or more physical processors, a second inspiratory flow rate during the one or more breathing cycles with the reduced pressure level, and further determining the classification of the breathing disorder of the subject based on a change between the first inspiratory flow rate and the second inspiratory flow rate.

8. The method of claim 5, further comprising:

repeatedly increasing, with the one or more physical processors and the pressure generator, the pressure level of the pressurized flow with respect to the recommended EPAP level during expirations for one or more breathing cycles;

determining, with the one or more physical processors, whether stability of the airway has been restored based on the generated output signals; and further determining the classification of the breathing disorder of the subject based on an amount the pressure level is increased during expirations.

9. A pressure support system configured to provide pressure support to an airway of a subject, the system comprising:

a pressure generator configured to provide a pressurized flow of breathable gas at a pressure level to the airway of the subject;

a subject interface configured to conduct the pressurized flow of breathable gas to the airway of the subject, the subject interface including an interface appliance configured to removably engage the airway of the subject;

one or more sensors in fluid communication with the subject interface and configured to generate output signals conveying information related to breathing of the subject; and one or more physical processors configured to:

control the pressure generator based on the output signals to generate the pressurized flow at an inspiration pressure level during inspirations of the subject and at an expiration pressure level during expirations of the subject;

control the pressure generator to repeatedly reduce the pressure level of the pressurized flow from the inspiration pressure level during successive inspirations of the subject, until the output signals indicate airway instability of the subject;

determine, based on the output signals, a reduction amount of the pressure level resulting from the repeated reduction that caused the airway instability; and determine a classification of a breathing disorder of the subject based on the reduction amount of the pressure level that caused the airway instability.

10. The pressure support system of claim 9, wherein the one or more physical processors are further configured to:

determine a first inspiratory flow rate during a first inspiration of the subject;

determine a second inspiratory flow rate during a second inspiration of the subject, the pressure level of the pressurized flow of breathable gas being lower during the second inspiration relative to the first inspiration; and further determine the classification of the breathing disorder of the subject based on a difference between the first inspiratory flow rate and the second inspiratory flow rate.

11. The pressure support system of claim 10, wherein the one or more physical processors are configured such that the difference between the first inspiratory flow rate and the second inspiratory flow rate is a difference in a shape of an inspiratory flow rate curve for the second inspiration of the subject relative to the first inspiration of the subject.

12. The pressure support system of claim 9, wherein the one or more physical processors are further configured to:

determine a delay parameter that indicates a delay between an onset of a given inspiration of the subject and a change in an inspiratory flow rate that corresponds to the onset of the given inspiration of the subject; and further determine the classification of the breathing disorder of the subject based on the delay parameter.

* * * * *